(12) United States Patent
Sassi et al.

(10) Patent No.: US 10,880,625 B2
(45) Date of Patent: Dec. 29, 2020

(54) SELF-POWERED MICROSENSORS FOR IN-SITU SPATIAL AND TEMPORAL MEASUREMENTS AND METHODS OF USING SAME IN HYDRAULIC FRACTURING

(71) Applicants: Khalifa University of Science And Technology, Abu Dhabi (AE); ABU DHABI COMPANY FOR ONSHORE PETROLEUM OPERATION LIMITED, Abu Dhabi (AE)

(72) Inventors: Mohamed Ben Mahmoud Sassi, Moknine (TN); Manhal Sirat, Uppsala (SE); Irfan Abdulqayyum Saadat, Santa Clara, CA (US); Rashid Kamel Abu Al-Rub, Amman (JO)

(73) Assignees: Khalifa University of Science And Technology, Abu Dhabi (AE); ABU DHABI COMPANY FOR ONSHORE PETROLEUM OPERATION LIMITED, Abu Dhabi (AE)

( * ) Notice: Subject to any disclaimer, the term of this patent is extended or adjusted under 35 U.S.C. 154(b) by 0 days.

(21) Appl. No.: 16/204,301

(22) Filed: Nov. 29, 2018

(65) Prior Publication Data
US 2019/0273973 A1 Sep. 5, 2019

Related U.S. Application Data

(63) Continuation of application No. 14/713,130, filed on May 15, 2015, now abandoned.
(Continued)

(51) Int. Cl.
*H04Q 9/00* (2006.01)
*E21B 43/26* (2006.01)
(Continued)

(52) U.S. Cl.
CPC ............... *H04Q 9/00* (2013.01); *A61B 5/05* (2013.01); *E21B 41/0085* (2013.01);
(Continued)

(58) Field of Classification Search
CPC ...... E21B 43/26; E21B 41/0085; E21B 47/00; E21B 47/06; H04Q 9/00
(Continued)

(56) References Cited

U.S. PATENT DOCUMENTS 6,324,904 B1  12/2001  Ishikawa et al.
6,443,228 B1   9/2002  Aronstam et al.
(Continued)

OTHER PUBLICATIONS

PCT International Search Report dated Oct. 8, 2015, received in corresponding PCT Application No. PCT/IB15/00701, 12 pgs.
(Continued)

*Primary Examiner* — Nimeshkumar D Patel
*Assistant Examiner* — Jean F Morello
(74) *Attorney, Agent, or Firm* — Billion & Armitage; Gregory S. Schwartz

(57) ABSTRACT

A delayed-activation sensor system includes at least one microsensor. The microsensor may include at least one sensor module for sensing a condition in an environment and a dissolvable coating encapsulating at least a portion of the at least one sensor module such that the dissolvable coating prevents the at least one sensor module from sensing the condition in the environment. The dissolvable coating may be dissolvable in a fluid in the environment such that the sensor module is activated after being located in the environment for a period of time. The microsensor may also include at least one energy harvester module to generate electrical power for the microsensor from the environment.

18 Claims, 9 Drawing Sheets

Related U.S. Application Data

(60) Provisional application No. 61/994,274, filed on May 16, 2014.

(51) Int. Cl.
| | | |
|---|---|---|
| *E21B 43/267* | (2006.01) | |
| *E21B 47/06* | (2012.01) | |
| *E21B 47/12* | (2012.01) | |
| *A61B 5/05* | (2006.01) | |
| *E21B 41/00* | (2006.01) | |
| *E21B 47/00* | (2012.01) | |
| *E21B 47/07* | (2012.01) | |
| *E21B 47/11* | (2012.01) | |
| *E21B 47/13* | (2012.01) | |
| *E21B 47/26* | (2012.01) | |

(52) U.S. Cl.
CPC ............ *E21B 43/26* (2013.01); *E21B 43/267* (2013.01); *E21B 47/00* (2013.01); *E21B 47/06* (2013.01); *E21B 47/07* (2020.05); *E21B 47/11* (2020.05); *E21B 47/12* (2013.01); *E21B 47/13* (2020.05); *E21B 47/26* (2020.05); *H04Q 2209/886* (2013.01)

(58) Field of Classification Search
USPC ...................................................... 73/152.39
See application file for complete search history.

(56) References Cited

U.S. PATENT DOCUMENTS

| | | | |
|---|---|---|---|
| 6,889,165 B2 | 5/2005 | Lind et al. | |
| 7,112,752 B1 | 9/2006 | Wenner | |
| 8,583,227 B2 | 11/2013 | Savage et al. | |
| 2002/0120186 A1 | 8/2002 | Keimel | |
| 2007/0044958 A1 | 3/2007 | Rytlewski et al. | |
| 2010/0102986 A1* | 4/2010 | Benischek | E21B 47/121 340/855.8 |
| 2011/0132620 A1 | 6/2011 | Agrawal et al. | |
| 2012/0004527 A1 | 1/2012 | Thompson et al. | |
| 2012/0037368 A1* | 2/2012 | Eick | C09K 8/516 166/300 |
| 2013/0118733 A1 | 5/2013 | Kumar | |
| 2013/0213647 A1 | 8/2013 | Roddy et al. | |
| 2014/0251600 A1* | 9/2014 | Scott | E21B 47/00 166/250.01 |
| 2014/0299783 A1* | 10/2014 | Valentino | G01J 1/0488 250/394 |
| 2016/0222284 A1* | 8/2016 | He | C09K 8/86 |
| 2016/0265307 A1* | 9/2016 | Stanciu | C09K 8/575 |

OTHER PUBLICATIONS

PCT Written Opinion dated Oct. 8, 2015, received in corresponding PCT Application No. PCT/IB15/00701, 6 pgs.

Ickes, N. et al, "Self-powered Long-range Wireless Microsensors for Industrial Applications", MTL Annual Research Report 2013, Microsystems Technology Laboratories, Mass Institute of Technology, Cambridge, MA, 2013, pp. 1-3.

Extended Search Report dated Mar. 1, 2018, issued in European Patent Application No. 15892496.9, 7 pages.

\* cited by examiner

SELF-POWERED MICROSENSORS FOR IN-SITU SPATIAL AND TEMPORAL MEASUREMENTS AND METHODS OF USING SAME IN HYDRAULIC FRACTURING

PRIORITY

This application is a continuation of U.S. patent application Ser. No. 14/713,130, filed May 15, 2015, which claims benefit under 35 U.S.C. § 119(e) to U.S. Provisional Patent Application No. 61/994,274 entitled "SELF-POWERED MICROSENSORS FOR IN-SITU SPATIAL AND TEMPORAL MEASUREMENTS AND METHODS OF USING SAME IN HYDRAULIC FRACTURING" filed May 16, 2014, all of which are incorporated herein, in entirety, by reference.

TECHNICAL FIELD

The present invention relates to microsensors and more particularly, to microsensors for in-situ spatial and temporal measurements and methods of using same in hydraulic fracturing.

BACKGROUND INFORMATION

Sensors are used in a wide range of applications for measuring various conditions. Designing sensors that are capable of operating and obtaining the desired measurements in certain environments and applications may be a challenge. In some applications, for example, the sensors must be a small size to be positioned in the environment where the conditions are to be measured. Sensors may also be damaged by environmental factors, such as high temperatures, high pressures, and corrosive materials.

One application where sensing various conditions is desirable, but difficult, is hydraulic fracturing. Hydraulic fracturing is the fracturing of rock by a pressurized liquid and is commonly known as "fracking." Typically, hydraulic fracturing involves two steps. In the first step, water is mixed with sand and chemicals, and the mixture is injected at high pressure (e.g., 1500 to 3000 PSI) into a wellbore to create small fractures (typically around several mm in width). Fluids such as gas, petroleum, uranium-bearing solution, and brine water may migrate along these fractures to the well. In the second step, the hydraulic pressure is removed from the well, and small grains or particles of proppant (e.g., sand or aluminum oxide) are injected to hold these fractures open once the rock achieves equilibrium. The proppants may include spherical balls with a radius of 3-4 mm and made of ceramic and/or other hard materials. Because of the size and shape of the proppants, fluid may diffuse out of the fractures or cracks.

BRIEF DESCRIPTION OF THE DRAWINGS

These and other features and advantages will be better understood by reading the following detailed description, taken together with the drawings wherein.

DETAILED DESCRIPTION

Microsensors, consistent with embodiments disclosed herein, may be used for in-situ spatial and temporal measurements. According to one aspect, the microsensors may include self-powered microsensors. As used herein, "self-powered" refers to the capability of the microsensor to generate sufficient power to operate the electronics in the microsensor, for example, by harvesting energy in the environment. Embodiments of self-powered microsensors generally include one or more sensor elements for measuring conditions, data processing circuitry for processing data (e.g., sensor data from the sensor elements and/or location data from other microsensors or transmitters), circuitry for storing, transmitting and/or receiving data, and an energy harvester for self-powering the sensor elements and circuitry. As will be described in greater detail below, the microsensor design (e.g., the types of sensor elements, the type of energy harvester, or the type of circuitry) may depend on the particular application for the microsensor.

Figure 1:
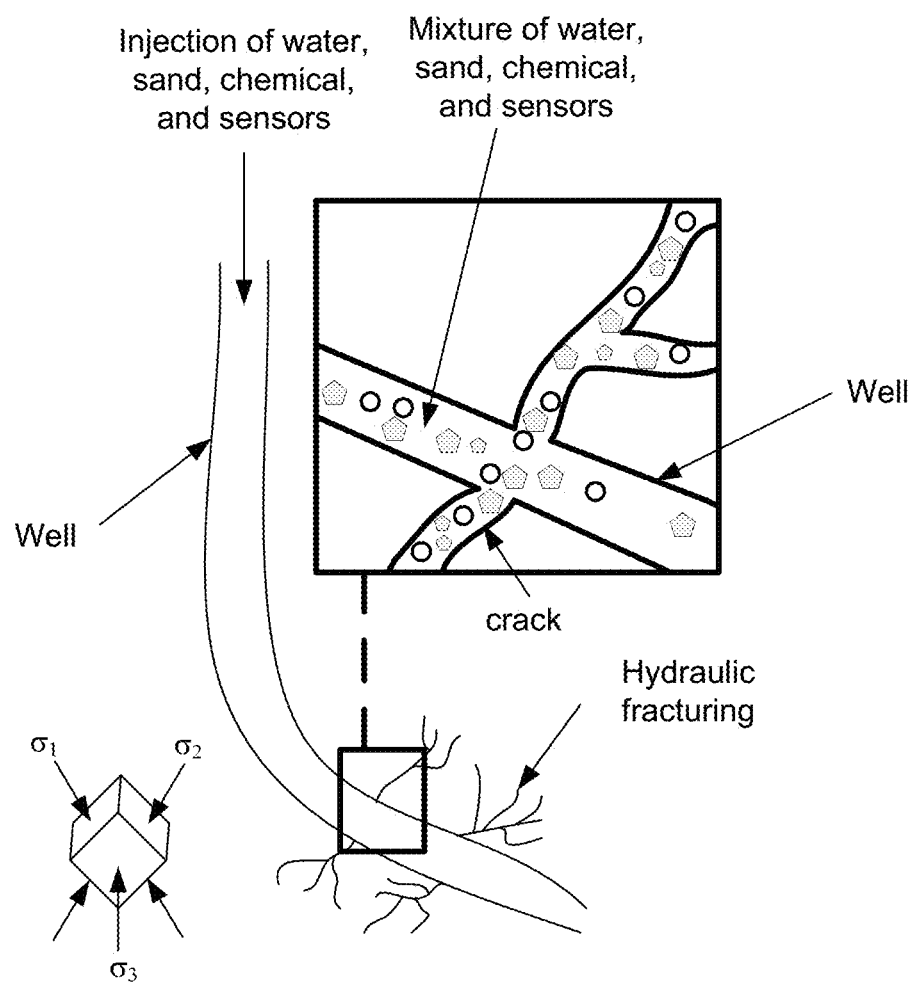
FIG. 1 is a schematic diagram of microsensors being injected into a well during a hydraulic fracturing operation, consistent with an embodiment of the present disclosure.

A plurality of self-powered microsensors may be used together for measuring conditions at locations throughout an environment being monitored and/or for mapping the environment. For example, a plurality of self-powered microsensors 10a-n may be used for measurements during and after hydraulic fracturing (also referred to as "fracking"). As shown in FIG. 1, a plurality of self-powered microsensors 10a-n may be injected into a well bore 12. The microsensors 10a-n may be injected (e.g., introduced) into the well bore 12 together with a fluid 14 for monitoring the dynamics of the fracturing process. The microsensors 10a-n may be used, for example, with tomography techniques to map the shape of the reservoir before, during, and/or after the fracking process.

According to one aspect, the fluid 14 with which the microsensors 10a-n may be introduced into the well bore 12 may include, but is not limited to, a fracking mixture. The fracking mixture may include any fracking mixture known to those skilled in the art for creating fractures in the rock under high pressure. By way of example, the fracking mixture may include a mixture of water and chemical additives. The chemical additives may include, but are not limited to, one or more of the following:

Acids (such as, but not limited to, Hydrochloric acid (HCl, 3% to 28%) and/or muriatic acid) configured to clean up perforation intervals of cement and drilling mud prior to fracturing fluid injection and provide accessible path to formation.

Breakers (such as, but not limited to, peroxydisulfates) configured to reduce the viscosity of the fluid in order to release proppant into fractures and enhance the recovery of the fracturing fluid.

Bactericides/Biocides (such as, but not limited to, gluteraldehyde and/or 2-bromo-2-nitro-1,2-propanediol) configured to inhibit growth of organisms that could produce gases (particularly hydrogen sulfide) that could contaminate methane gas and/or also configured to prevent the growth of bacteria which can reduce the ability of the fluid to carry proppant into the fractures.

Buffers/pH Adjusting Agents (such as, but not limited to, sodium or potassium carbonate and/or acetic acid) configured to adjust and/or control the pH of the fluid in order to maximize the effectiveness of other additives, such as crosslinkers discussed herein.

Clay Stabilizers/Controls (such as, but not limited to, salts including tetramethyl ammonium chloride and/or potassium chloride) configured to prevent swelling and/or migration of formation clays which could block pore spaces thereby reducing permeability.

Corrosion Inhibitors (such as, but not limited to, methanol and/or ammonium bisulfate for oxygen scavengers) configured to reduce rust formation on steel tubing, well casings, tools, and tanks (generally used in fracturing fluids that contain acid).

Crosslinkers (such as, but not limited to, potassium hydroxide and/or borate salts). The fluid viscosity may be increased using phosphate esters combined with metals. The metals may be referred to as crosslinking agents. The increased fracturing fluid viscosity may allow the fluid to carry more proppant into the fractures.

Friction Reducers (such as, but not limited to, sodium acrylate-acrylamide copolymer, polyacrylamide (PAM), and/or petroleum distillates) configured to allow fracture fluids to be injected at optimum rates and pressures by minimizing friction.

Gelling Agents (such as, but not limited to, guar gum and/or petroleum distillate) configured to increase fracturing fluid viscosity, allowing the fluid to carry more proppant into the fractures.

Iron Controls (such as, but not limited to, ammonium chloride, ethylene glycol, and/or polyacrylate) configured to prevent the precipitation of carbonates and sulfates (calcium carbonate, calcium sulfate, barium sulfate) which could plug off the formation.

Solvents (such as, but not limited to, aromatic hydrocarbons) which may include one or more additives that are soluble in oil, water & acid-based treatment fluids that are used to control the wettability of contact surfaces or to prevent or break emulsions.

Surfactants (such as, but not limited to, methanol, isopropanol, and/or ethoxylated alcohol) configured to reduce fracturing fluid surface tension thereby aiding fluid recovery.

Figure 2:
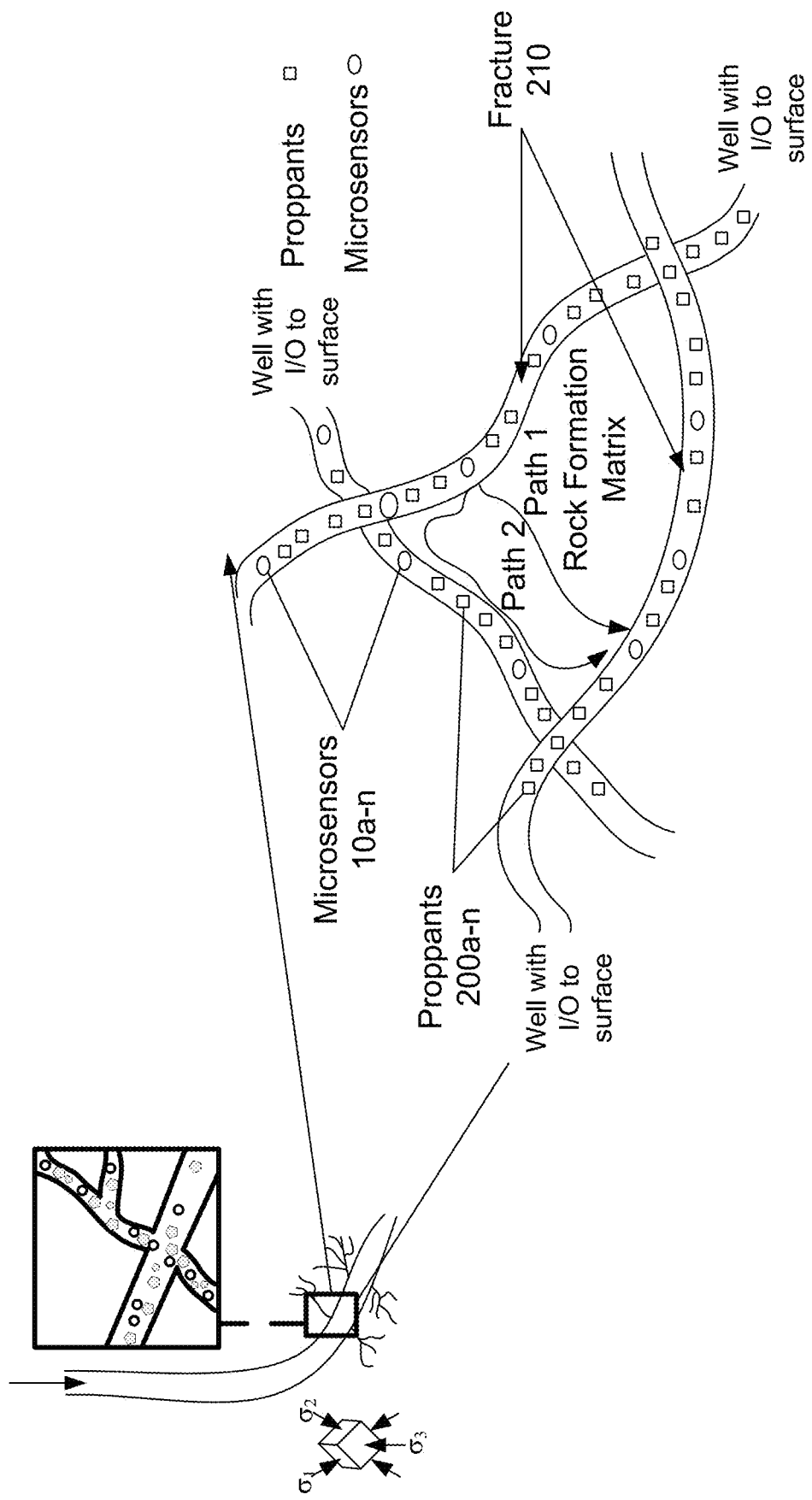
FIG. 2 is a schematic diagram of microsensors located in fractures formed by the hydraulic fracturing operation, consistent with an embodiment of the present disclosure.

As shown in FIG. 2, a plurality of self-powered microsensors 10a-n may also be injected together with proppants 200a-n (e.g., after the fracking process) into the fractures or cracks 210 after the fracturing occurs to monitor production of oil and/or for measuring conditions, such as temperature, pressure, and presence of oil. The proppants 200a-n may include any material(s) configured to be embedded into and/or keep fractures/cracks open to allow gas/fluids to flow more freely to the well bore. The proppants 200a-n may include, but are not limited to, one or more of sand (including sintered bauxite, zirconium oxide) and/or ceramic beads. It should be appreciated that the proppants 200a-n and microsensors 10a-n may be separate from, or included in, the fracking mixture 14. The microsensor 10a-n may have a size and shape consistent with the form factor of the proppants 200a-n, for example, a spheroid or spherical shape may range from 1 mm to 20 mm in size.

As discussed herein, the plurality of self-powered microsensors 10a-n may be configured to generate wireless signals (e.g., ping signals such as, but not limited to, an RF electromagnetic wave) which includes the sensor collected data. The ping signals may optionally include a unique ID and/or location parameters. The microsensors 10a-n may transmit ping signals periodically (e.g., at fixed time intervals such as, but not limited to, 5 minutes) and/or based on one or more threshold values (e.g., a power supply threshold and/or buffer threshold). For example, the microsensors 10a-n if the power supply is below a threshold, the microsensors 10a-n may wait until the power supply reaches and/or exceeds the power supply threshold. Alternatively (or in addition), the microsensors 10a-n may wait until the data stored in a buffer and/or memory (e.g., sensor data from one or more microsensors 10a-n) reaches and/or exceeds a buffer/memory threshold.

Figure 3:
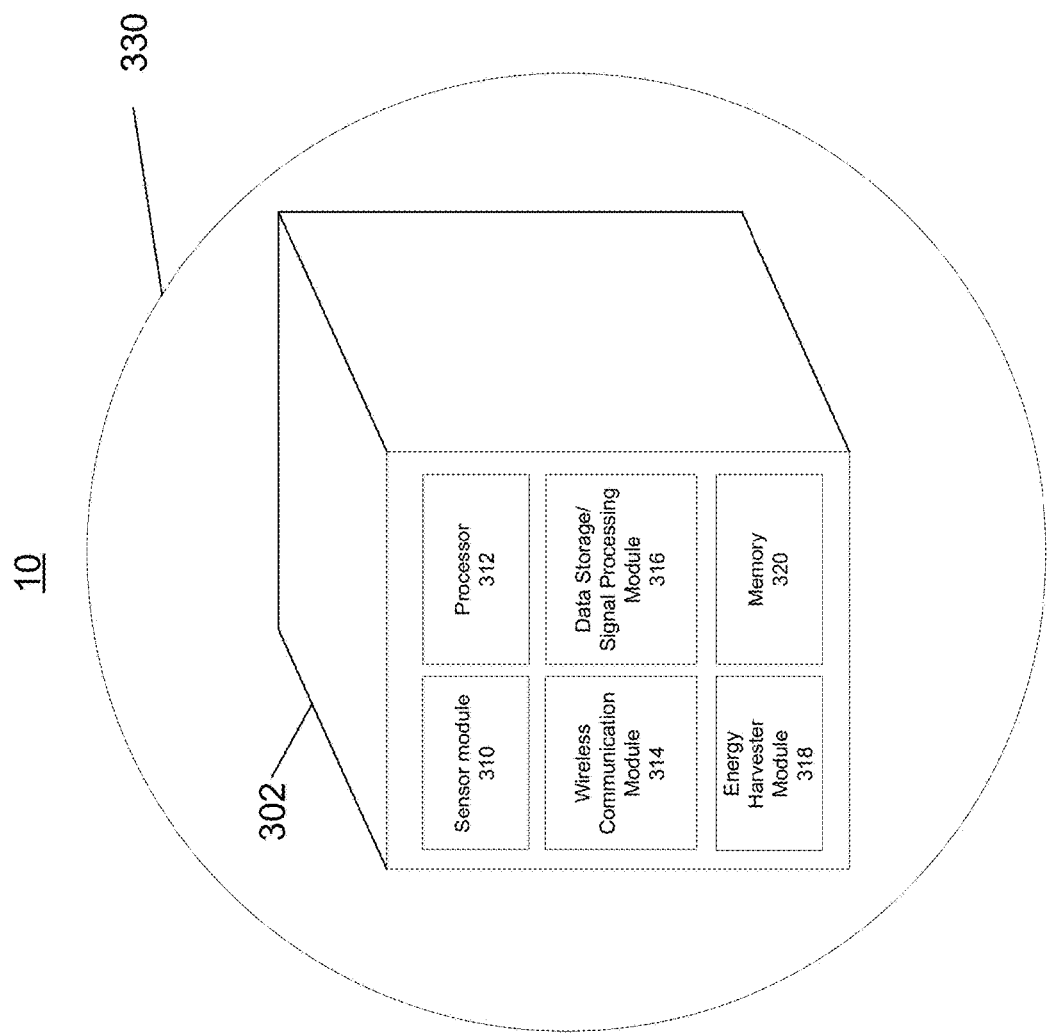
FIG. 3 is a perspective view of microsensors consistent with at least one embodiment of the present disclosure.

As shown in FIG. 3, one aspect of an individual microsensor 10 consistent with the present disclosure is generally illustrated. The microsensor 10 may include one or more sensor modules 310, at least one processing circuitry 312 (e.g., but not limited to, one or more CPUs, circuitry, processors, logic, or the like), at least one wireless communication module 314, at least one data storage/signal processing module 316, at least one energy harvester module 318, and/or at least one memory 320. The microsensor 10 also include a support body/structure 302 configured to support sensor modules 310, processing circuitry 312, wireless communication module 314, data storage/signal processing module 316, energy harvester module 318, and/or memory 320. It should be appreciated that the microsensor 10 shown in FIG. 3 is for illustrative purposes, and that one of ordinary skill in the art (upon reading the present disclosure as a whole) will understand that various functions and/or components may be combined and/or eliminated.

An individual microsensor 10 may include cubical or cuboid shaped structure, though other shapes are possible such as, but not limited to, spherical, oblong, and the like. One or more microsensors 10a-n may be covered and/or encapsulated with a coating as described herein. The coating may have a form a spherical or spheroid shaped. As used herein, a the terms "cube," "cubical," and "cuboid" do not require a perfect cube shape and the terms "sphere," "spherical," and "spheroid" do not require a perfect sphere shape. To be compatible with high temperatures and a harsh environment, the microsensor 10, and/or portions thereof, may be made out of graphene, carbon nanotubes and/or similar materials. These materials have demonstrated thermal stability up to 700° C. and also are chemically inert such that they can detect the presence of other materials without chemically reacting with them. For higher temperature requirements, sensors made from GaN be used, which can withstand temperatures up to ~900 C.

The sensor module 310 may include one or more sensors and/or sensor arrays. The sensors may include, without limitation, temperature sensor elements, pressure sensor elements, stress sensor elements, pH sensor elements, and chemical composition sensor elements. The sensor module 310 may include a sensor array with sensors tuned to detect the target physical and chemical properties of the environment in the fractures or cracks. The target physical properties may include pressure and/or stress in the rock formation and other environmental properties in steady state/production. With reference to FIG. 1, a cubical or cuboid shaped microsensor 10 may be capable of measuring stress in three axes (e.g., σ1, σ2, and σ3), for example, by using sensor elements on at least three faces of the cuboid structure. To be compatible with high temperature and a harsh environment, these sensors may also be made out of GaN, graphene, carbon nanotubes and similar materials. These materials have demonstrated thermal stability from 700° C. (in case of carbon nanomaterials) to 900° C. (in case of GaN). The carbon nanomaterials are chemically inert such that they can detect the presence of other materials without chemically reacting with them.

Referring back to FIG. 3, the processing circuitry 312 may be configured to process and cause data to be stored, for example, in memory 320 (such as, but not limited to, a buffer or the like). For example, the processing circuitry 312 may be configured to process data generated by the sensor module 310 with time data (e.g., time data corresponding to sensor data generated by the sensor module 310), sensor type data (e.g., data associated with and/or identifying each sensor and/or type of sensor in the sensor module 310), location data corresponding to the position/location of the microsensor 10, and/or microsensor identification data which uniquely identifies the microsensor 10, and cause one or more of the data to be stored in the memory 320. The processing circuitry 312 may also be configured to determine and/or approximate the position of the microsensor 10. For example, processing circuitry 312 may also be configured to provide telemetry and/or triangulation based on pinging signals to or from two probes (e.g., in two wells) and/or other location based signals.

In this embodiment, the processing circuitry 312 may include high temperature electronics based circuits capable of operating on low power. High temperature electronics can be made out of GaN, which can operate in temperatures up to 900° C., and silicon on insulator (SOI) circuits, which can operate in temperatures up to 200° C. The processing circuitry 312 may be configured to receive the data from the sensor module 310, wireless communication module 314, data storage/signal processing module 316, and/or memory 320, processes the data, and sends the data to a storage element (e.g., memory 320) and/or the wireless communication module 314. The data may be used to create temporal and spatial map for a given property or metric during the fracking process. Processing circuitry 312 may also process data for telemetry and/or triangulation based on an external pinging signal.

A communication module 314 may be configured to cause one or more signals to be transmitted. For example, the communication module 314 enables wireless communications for the transfer of data to and/or from the microsensor 10 to one or more microsensors, nodes, supersensors, collection/processing controllers, and/or external devices. The term "wireless" and its derivatives may be used to describe circuits, devices, systems, methods, techniques, communications channels, etc., that may communicate data through the use of modulated electromagnetic radiation through a non-solid medium.

Communication module 314 may implement any of a number of wireless standards or protocols, including, but not limited to, Wi-Fi (IEEE 802.11 family), WiMAX (IEEE 802.16 family), IEEE 802.20, long term evolution (LTE), Ev-25 DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. Communication modules 314 may therefore include hardware to support wireless communication, e.g., one or more transponders, antennas, BLUETOOTH chips, personal area network chips, near field communication chips, wired and/or wireless network interface circuitry, combinations thereof, and the like. The micro sensor 10 may include a plurality of communication modules 314. For instance, a first communication module 314 may be dedicated to shorter range wireless communications such as Wi-Fi and Bluetooth and a second communication module 314 may be dedicated to longer range wireless communications such as GPS, EDGE, GPRS, CDMA, WiMAX, LTE, Ev-DO, and others.

The communication module 314 may be capable of sensing (e.g., receiving) acoustic pinging signals or RF beacons for telemetry applications. In addition or alternatively, the communication module 314 may be capable of transmitting a pinging signal. For example, the communication module 314 may be configured to transmit one or more pinging signals to fixed locations to provide a triangulation capability for obtaining location data.

The data storage/signal processing module 316 may be configured to store and/or process data. For example, the data storage/signal processing module 316 may be configured to store data generated by the sensor module 310, processed by the processing circuitry 312, and/or received by the communication module 314. According to one aspect, the data storage/signal processing module 316 may store data from a plurality of different sources (e.g., but not limited to, the sensor module 310, the processing circuitry 312, and/or the communication module 314) and/or store data from one or more sources over time until a threshold amount of data and/or time period has been reached and/or exceeded. The data storage/signal processing module 316 may also be configured to cause the collected/stored data to be consolidated into one or more ping signals. For example, the data storage/signal processing module 316 may be configured to cause the collected data to be stored in a single packet (e.g., the payload of a single packet) of a ping signal that be may be transmitted by the communication module 314. The header of the ping signal may identify the destination address and/or the source of the ping signal. Depending on the size of the data to be transmitted, all of the data may not fit all within the payload of a single packet. As such, the data may be split and stored in two or more payloads of two or more packets.

The data storage/signal processing module 316 may also be configured to process and/or condition the data from one or more different sources (e.g., but not limited to, the sensor module 310, the processing circuitry 312, and/or the communication module 314). Non-limiting examples of processing and/or signal conditioning that the data storage/signal processing module 316 may perform include filtering, amplifying, signal-to-noise reduction, signal isolation, encoding, decoding, encryption, decryption, and/or the like. It may be appreciated that the data may also (or alternatively) be externally processed, for example, for purposes of creating an image using location data.

The energy harvester module 318 may harvest energy (also known as power harvesting or energy scavenging) from the environment such as kinetic energy, thermal energy, electromagnetic energy, salinity gradients, pH gradients, temperature gradients, and/or electrochemical energy and optionally store the energy (for example in one or more capacitors, super capacitors, batteries, and/or the like). A microsensor 10 may also include a self-contained energy source such as a thin film battery.

One example of an energy harvester module 318 includes electrochemical and/or thermoelectric generators (TEGs). TEGs may include two ore more dissimilar materials coupled together to form a junction in the presence of a thermal gradient. The voltage may be increased by connecting a plurality of junctions electrically in series and thermally in parallel. Thermal energy harvesters or electrochemical energy harvesters may be used. One example of a thermal energy harvester includes two different alloy metals, which produce a voltage drop when placed across a temperature gradient.

The energy harvester module 318 may include an electrochemical energy harvester. An electrochemical energy harvester may include dissimilar metals that form an electrochemical cell in the presence of ionic fluid in the environment in which they are used. If the microsensors 10 only include vibration based energy harvester modules 318, the microsensors 10 may become dormant after the fracking process until they are brought to the surface. If the microsensors 10 include thermal energy harvester modules 318 and/or electrochemical energy harvester modules 318, the microsensors 10 may be activated and powered when the microsensors 10 are stationary after the fracking process even without movement or vibrations.

Another example of an energy harvester module 318 includes piezoelectric crystals or fibers which generate a voltage whenever they are mechanically deformed. Vibration from the surrounding environment can stimulate piezoelectric materials, thereby generating an electrical current or voltage. For example, piezoelectric materials may convert mechanical strain into electric current or voltage. Vibration based energy harvester module 318 may take advantage of the vibration during the actual fracking process. Thus, the microsensors 10 may be energized as they move down the well and during the fracking process. One example of a vibration based energy harvester module 318 includes known energy harvesters based on AlN and capacitve sensors.

Yet another example of an energy harvester module 318 may include pyroelectric materials. Pyroelectric materials convert a temperature change into electric current or voltage. It is analogous to the piezoelectric effect, which is another type of ferroelectric behavior. Pyroelectricity requires time-varying inputs and may suffer from small power outputs in energy harvesting applications due to its low operating frequencies. However, one key advantage of pyroelectrics over thermoelectrics is that many pyroelectric materials are stable up to 1200° C. or higher, enabling energy harvesting from high temperature sources and thus increasing thermodynamic efficiency.

The energy harvester module 318 may include electrostatic (capacitive) energy harvesters. Electrostatic energy harvesting is based on the changing capacitance of vibration-dependent capacitors. Vibrations separate the plates of a charged variable capacitor, and mechanical energy is converted into electrical energy.

The energy harvester module 318 may include magnetic induction circuits. For example, movement of one or more magnets relative to one or more conductors may electrical currents due to Faraday's law of induction.

Yet a further example of an energy harvester module 318 may include metamaterial energy harvesters. Metamaterial-based energy harvesters wirelessly convert electrical signals (such as, but not limited to, microwave signals, RF signals, Wi-Fi signals, satellite signals, or even sound signals or the like) to electrical current (greater than that of a USB device).

Another example of an energy harvester module 318 includes electroactive polymers (EAPs). EAPs have a large strain, elastic energy density, and high energy conversion efficiency.

A further example of an energy harvester module 318 may include antennas configured to collect energy from stray radio waves. For example, the antennas may include a rectenna and/or a nantenna.

It should be appreciated that the microsensor 10 may replace the energy harvester module 318 with one or more batteries. It should also be appreciated that while the sensor module 310, processor 312, wireless communication module 314, data storage/signal processing module 316, energy harvester module 318, and memory 320 are illustrated as separate components, the functionality of one or more of these various components may be combined.

Memory 320 may be part of, and/or separate from, the data storage/signal processing module 316, and may be used to store data and/or applications/software to be executed by the processing circuitry 312.

According to one aspect, the microsensor 10 may optionally eliminate the wireless communication module 314, and instead may store all data generated by the sensor module 310 in memory and/or data storage/signal processing module 316. In particular, the microsensor 410 may be retrieved from the recirculated fluid after the fracking process and then read off-line to create an image/map of the well during the fracking dynamics. It should be appreciated, however, that the microsensor 10 may also include a wireless communication module 314 that can transmit the data to collection nodes, in addition to being configured to be read after being retrieved from the recirculated fluid.

The exterior of each of the microsensors 10 may be sealed and resistant to high temperatures and corrosion and the interior of the microsensors may include high temperature electronics/circuitry and components. In one embodiment, one or more coatings 330 may cover at least a portion of an exterior surface of the microsensor 10. According to one aspect, the one or more coatings 330 (either individually and/or collectively) may encapsulate the entire outer surface of the microsensor 10.

The coating 330 may be dissolvable and the microsensors 10 may be activated when the coating dissolves. For example, the coating 330 may dissolve due to temperature, pH, and/or contact with water, glycol, acids, breakers, buffers/pH adjusting agents, stabilizers, corrosion inhibitors, crosslinkers, friction reducers, gelling agents, iron controls, solvents, and/or surfactants as described herein. Non-limiting examples of dissolvable coatings 330 include polyamide, polyglycolide or polyglycolic acid, polyvinyl alcohol, polyvinyl pyrrolidone, polyethylene glycol, polystyrenesulfonate, quaternized amine polymers, alkoxomers, thermally decomposing polymer films, PC polymer, cellulose, hydroxyethylcellulose, ethylcellulose, cellulose esthers, resins, cationic polyacrylamide, acrylate, aminoacrylate, alkyl PEG-20, and mixtures thereof.

The dissolvable coating 330 may therefore be triggered by the chemical environment, a predetermined set temperature, and/or expose the underlying sensor elements and/or energy harvesters, thereby activating the microsensors. For example, the thermal dissolvable coating 330 may be selected from a group consisting of a polyamide, polyglycolide or polyglycolic acid, polyvinyl alcohol, polyvinyl pyrrolidone, polyethylene glycol, polystyrenesulfonate, quaternized amine polymers, alkoxomers, and mixtures thereof. A water dissolvable coating 330 may selected from a group consisting of a polymer, PC polymer, cellulose, hydroxyethylcellulose, ethylcellulose, cellulose esthers, resins, and mixtures thereof. A pH dissolvable coating 330 may selected from a group consisting of a cationic polyacrylamide, acrylate, aminoacrylate, alkyl PEG-20 and mixtures thereof According to one aspect, a plurality of microsensors 10 may be separately coated with dissolvable coatings 330. The coatings 330 on different microsensors 10 may dissolve at different times and/or under different conditions to provide staggered microsensor activation. The dissolvable coatings 330 may dissolve by using different materials and/or thicknesses to control the time for dissolving from 1 minute to 1 hour to 24 hours or longer. The dissolvable coatings 330 may thus allow a tunable activation, for example, in a range of 6-24 hours for each individual microsensor 10. The overall lifetime of a collective group of microsensors 10 may thus be extended by staggering the activation of subsets of the microsensors 10.

Figure 4:
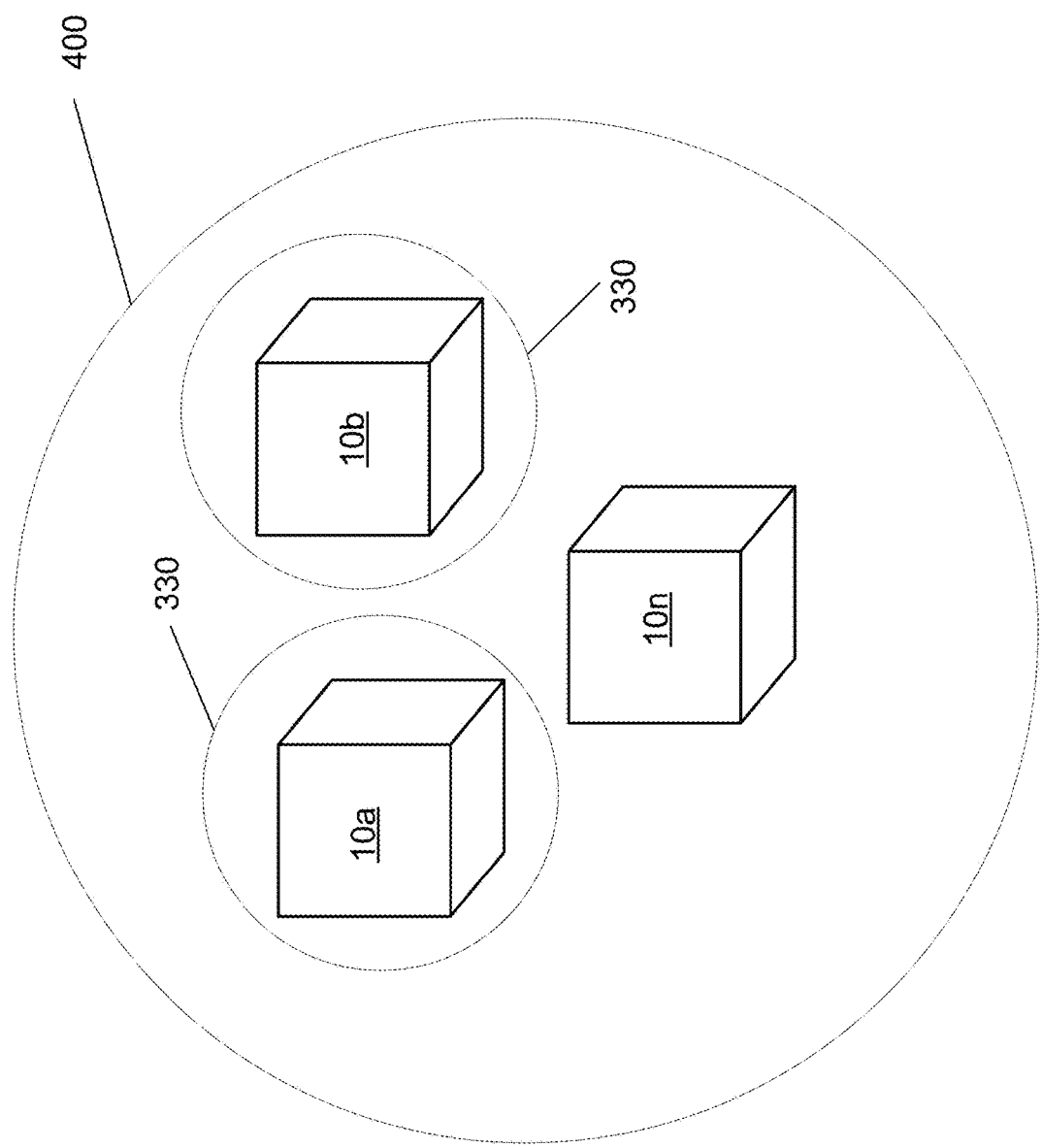
FIG. 4 is a perspective view of a plurality of microsensors encapsulated with a group coating.

It may be appreciated that a plurality of microsensors 10a-n may be combined and encapsulated by a coating 400 as generally illustrated in FIG. 4. The coating 400 may include one or more layers of material which may be the same and/or different. Additionally, one or more of the microsensors 10 (e.g., 10a, 10b) may have a separate coating covering 330. For example, a group coating 400 (which may include one or more layers of coating materials) may cover the plurality of microsensors 10a-n. Within the group coating 400, one or more microsensors 10a, 10b may include an individual coating 330 (which may include one or more layers of coating materials). The group coating 400 may dissolve to expose one or more microsensors (e.g., 10n) and/or individual coatings 330 covering one or more microsensors (10a, 10b). The individual coatings 330 may then dissolve based on different conditions than the group coating 400.

Figure 5:
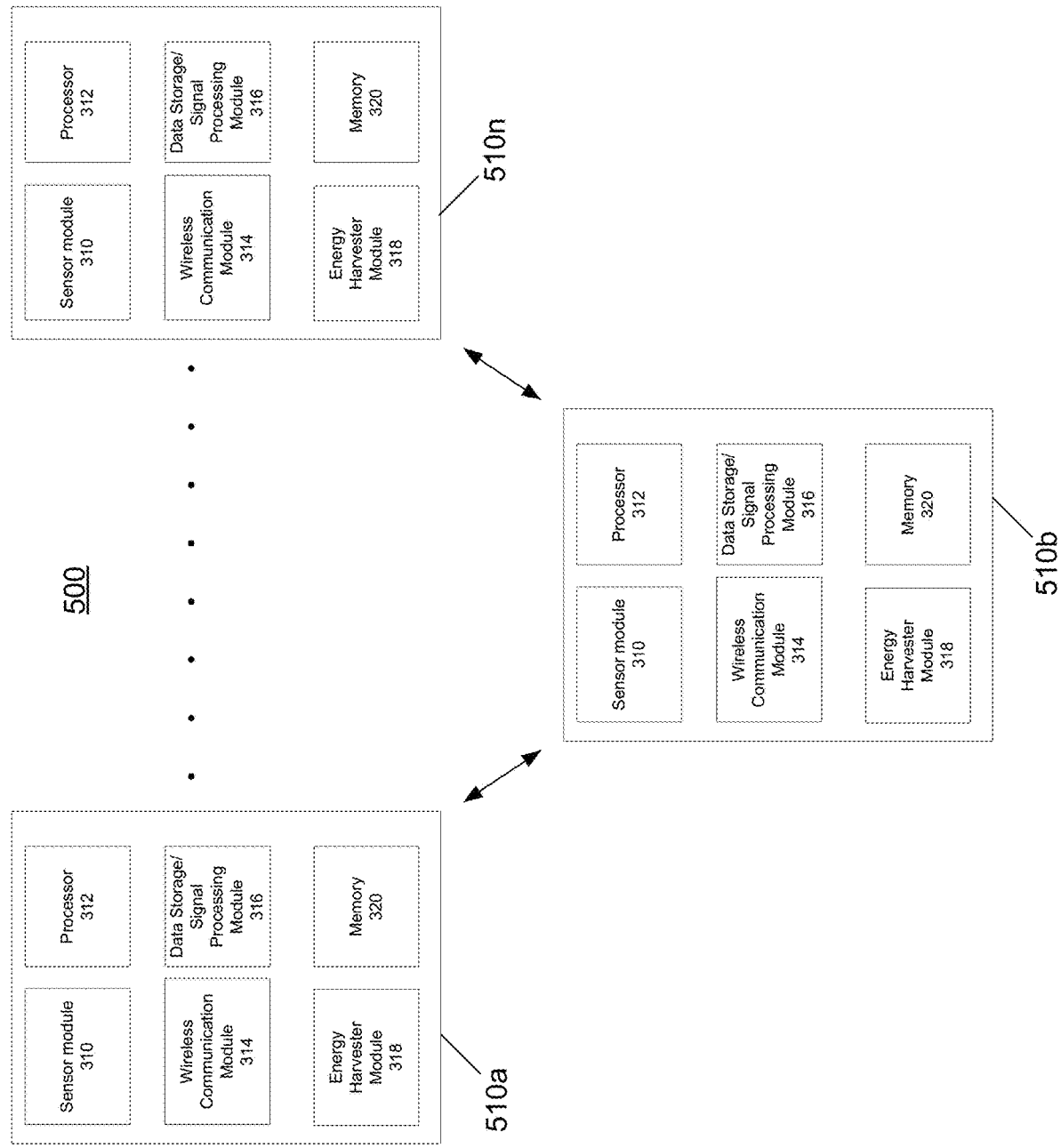
FIG. 5 is a schematic diagram of a system/network of microsensor nodes comprising a plurality of microsensors.

According to one aspect, a plurality of the microsensors 510a-n, FIG. 5, may communicate with each other to form a system/network of microsensor nodes 500 (e.g., the microsensors 510a-n may operate as nodes in a sensor network 500). For example, the microsensors 510a-n may be configured to transmit a ping signal to adjacent microsensors 510a-n. A microsensor 510a-n which receives a ping signal from an adjacent microsensor 510a-n may be configured to retransmit the ping signal of the adjacent microsensor 510a-n, along with its own ping signal. The process may be continued until the ping signals are received by a controller. The microsensors 510a-n may be configured to determine the shortest communication path to one or more collection/processing controllers, for example, based on their location data and/or unique identifier. As may be appreciated, the ability to determine the shortest transmission communication path(s) may allow the wireless communication module of the microsensor 510a-n to transmit a lower strength/power ping signal, thereby reducing the power requirements of the microsensors 510a-n. Additionally (or alternatively), the microsensors 10a-n may be configured to retransmit up to a predetermined number of ping signals in order to avoid overloading any one particular microsensor 510a-n, thereby reducing the power requirements of the microsensors 510a-n. As discussed herein, the microsensors 510a-n may be configured to either periodically transmit/retransmit the ping signals and/or may transmit/retransmit the ping signals upon reach a threshold (e.g., supply power and/or buffer thresholds).

Figure 6:
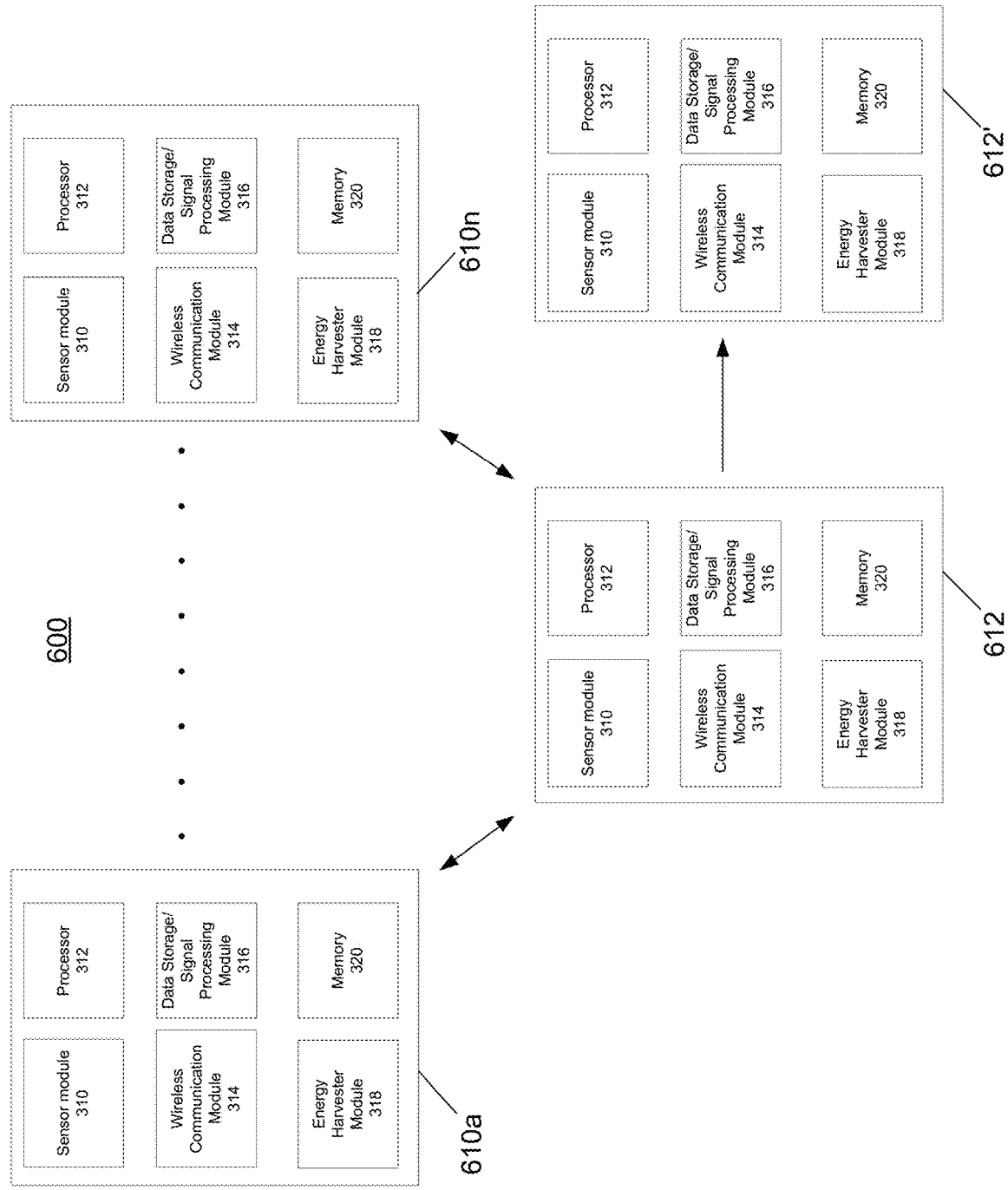
FIG. 6 is a schematic diagram of a supersensor/satellite sensor system.

Turning now to FIG. 6, one configuration of supersensor/satellite sensor system 600 is generally illustrated. The supersensor/satellite sensor system 600 may include one or more (e.g., a plurality of) satellite microsensors 610a-n in communication with one or more supersensor microsensors 612. As discussed herein, the supersensors 612 may form the backbone in the supersensor/satellite sensor system 600 through which data transmitted by their respective satellite sensors 610a-n is collected, processed and transmitted. For example, the satellite sensors 610a-n may be configured to generate and transmit ping signals including the sensor data and optionally location information and/or a unique identifier. The plurality of satellite sensors and/or supersensors may include, but not limited to, sensing functions like temperature, pH, pressure (e.g., but not limited to, pore-water pressure), stress, magnetic field strength, chemical composition, and/or various stresses within the fractured rock and any formation change data as described herein.

The supersensor 612 may be similar to the satellite sensors 610a-n, except that the supersensor 612 may be configured to receive and/or store the ping signals from nearby satellite sensors 610a-n (e.g., in a larger memory than the satellite sensors 610a-n), and retransmit the ping signals from nearby satellite sensors 610a-n along with its own ping signal. The supersensor 612 may therefore act a central node for a dedicated set of satellite sensors 610a-n, where a supersensor 612 collects and/or processes various parameters and measurements from the satellite sensors 610a-n. After collection, the supersensor 612 may be configured to transmit information through one or more additional supersensors 612' (if necessary). The supersensor 612 and other supersensors 612' in the chain are able transmit information to a receiving point outside the environment (e.g., collection/processing controllers), typically residing on the surface.

The satellite sensors 610a-n may therefore be configured to transmit the ping signals over a relatively short transmission range compared to the supersensor 612. As such, the power requirements for the satellite sensors 610a-n may be reduced compared to the supersensor 612. The reduced power requirements and transmission range of the satellite sensors 610a-n may allow the wireless communication module 314, energy harvester module 318, data storage/signal processing module 316, and/or memory 320 to be smaller and/or less expensive compared to the supersensor 512. The reduced size of the satellite sensors 610a-n compared to the supersensor 612 and/or regular microsensor 10 may allow the satellite sensors 610a-n to penetrate deeper in the rock formations which is beneficial in the case of fracking. According to one example, the supersensors 612 are of larger form factor ranging from 8 mm to 50 mm in size compared to the satellite sensor 610a-n which can be 1-20 mm in size. For example, the supersensor 612 may be 20 mm to 40 mm in size while the satellite sensor 610a-n may be 2-4 mm in size.

Figure 7:
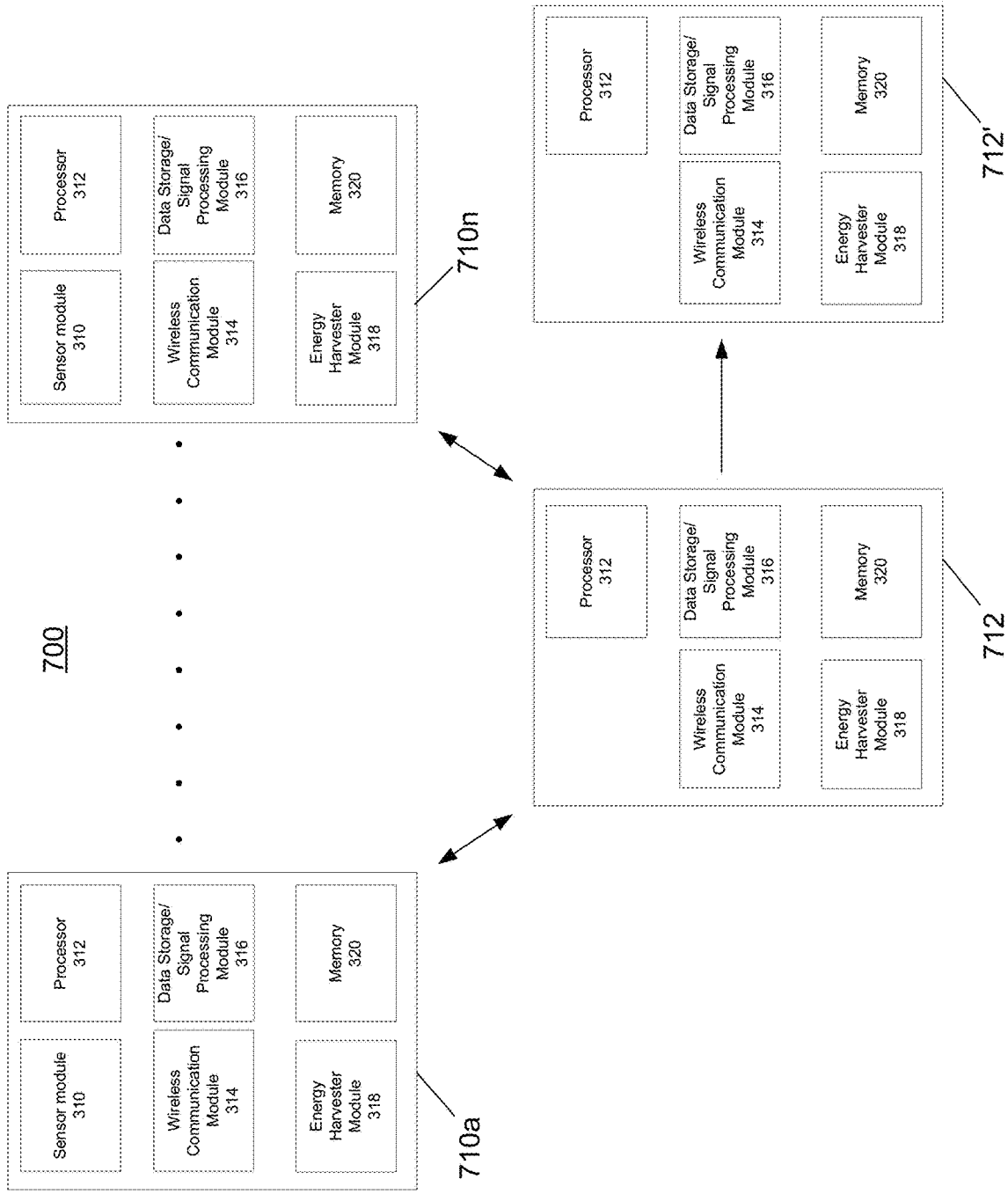
FIG. 7 is a schematic diagram of a satellite/node sensor system.

Turning now to FIG. 7, one configuration of satellite/node sensor system 700 is generally illustrated. The satellite/node sensor system 700 may include one or more (e.g., a plurality of) microsensors 710a-n in communication with one or more nodes 712. As discussed herein, the nodes 712 may form the backbone in the satellite/node sensor system 700 through which data transmitted by their respective microsensors 710a-n is collected, processed and transmitted. For example, the microsensors 710a-n may be configured to generate and transmit ping signals including the sensor data and optionally location information and/or a unique identifier. The fixed nodes and/or collection points may be introduced into the well bore 12 together with, or separate from, the microsensors 10a-n. The number of fixed nodes and/or collection points may be determined based on the wireless transmission range of the microsensors 10a-n, the number of microsensors 10*a-n*, and/or an estimate or expected distribution/location of the microsensors 10*a-n* within the well bore 12.

The nodes 712 may be similar to the satellite sensors 710*a-n*, except that the nodes 712 do not include a sensor module. As such, the nodes 712 are configured to receive and/or store the ping signals from nearby microsensors 710*a-n* (e.g., in a larger memory than the satellite sensors 710*a-n*), and retransmit the ping signals from nearby microsatellite sensors 710*a-n*. The nodes 712 may therefore act a central node for a dedicated set of microsatellite sensors 710*a-n*, where a node 712 collects and/or processes various parameters and measurements from the microsatellite sensors 710*a-n*. After collection, the nodes 712 may be configured to transmit information through one or more additional nodes 712' (if necessary). The nodes 712 and other nodes 712' in the chain are able transmit information to a receiving point outside the environment (e.g., collection/processing controllers), typically residing on the surface.

Again, similar to the supersensor/satellite sensor system 600, the microsatellite sensors 710*a-n* may therefore be configured to transmit the ping signals over a relatively short transmission range compared to the node 712. As such, the power requirements for the microsatellite sensors 710*a-n* may be reduced compared to the node 712. The reduced power requirements and transmission range of the microsatellite sensors 710*a-n* may allow the wireless communication module 314, energy harvester module 318, data storage/signal processing module 316, and/or memory 320 to be smaller and/or less expensive compared to the node 712. The reduced size of the microsatellite sensors 710*a-n* compared to the node 712 and/or regular microsensor 10 may allow the microsatellite sensors 710*a-n* to penetrate deeper in the rock formations which is beneficial in the case of fracking. Additionally, the cost of the nodes 712 may be reduced since they do not need to include a sensor module 310.

Figure 8:
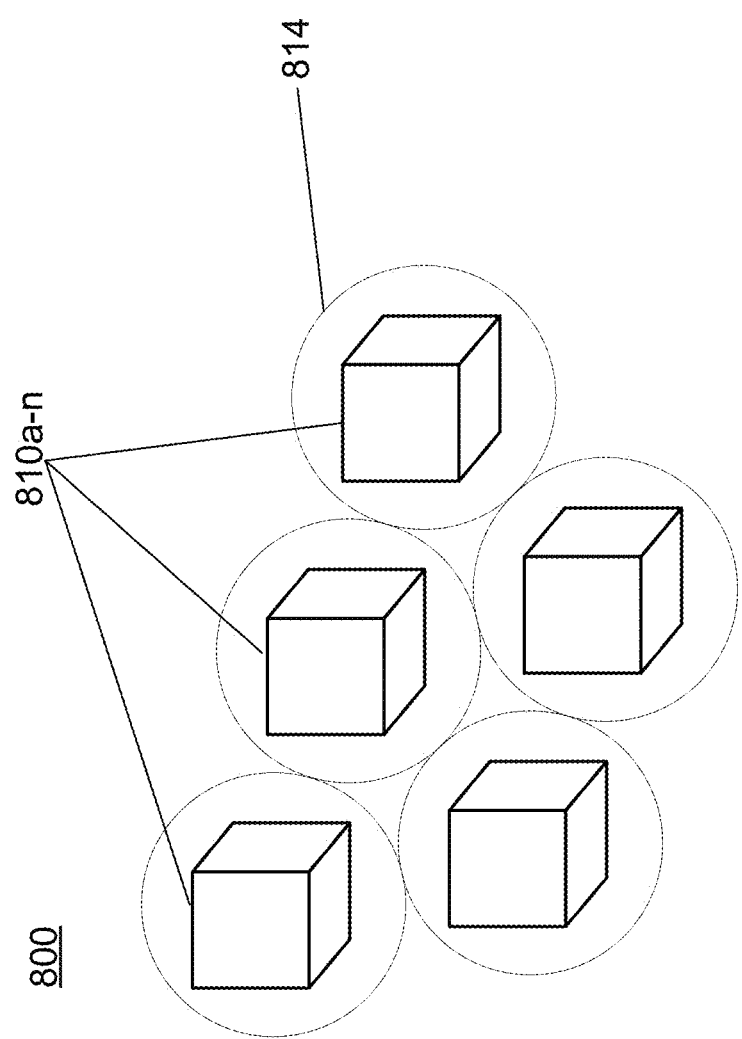
FIG. 8 is a schematic diagram of a plurality of microsensors forming a cluster system.

Referring to FIG. 8, one example of a system of microsensors consistent with the present disclosure is generally illustrated. The system may include a plurality of microsensors 810*a-n* that, once activated, may cluster together to form a single larger cluster 812. The cluster 812 microsensors 810*a-n* may aid in keeping the cracks open during and/or post fracking process. The cluster 812 may be achieved through one or more of electrostatic surface charge generation and/or surface coatings 814. For example, the electrostatic surface charge generation and/or surface coatings may use van der Waals forces that will allow the microsensors 810*a-n* to aggregate and/or stick together to form a cluster 812. Conversely, a cluster 812 of microsensors 810*a-n* that are coupled or attached together (e.g., with electrostatic force) can be fragmented into smaller sensors by aligning the surface polarity and making them the same for all sensors, thus creating repelling forces that will fragment the clusters. In other embodiments, similar aggregation may be accomplished using a supersensor where simple satellites sensors would adhere by providing a change in the surface polarity to attract and bind the simple satellites sensors.

Figure 9:
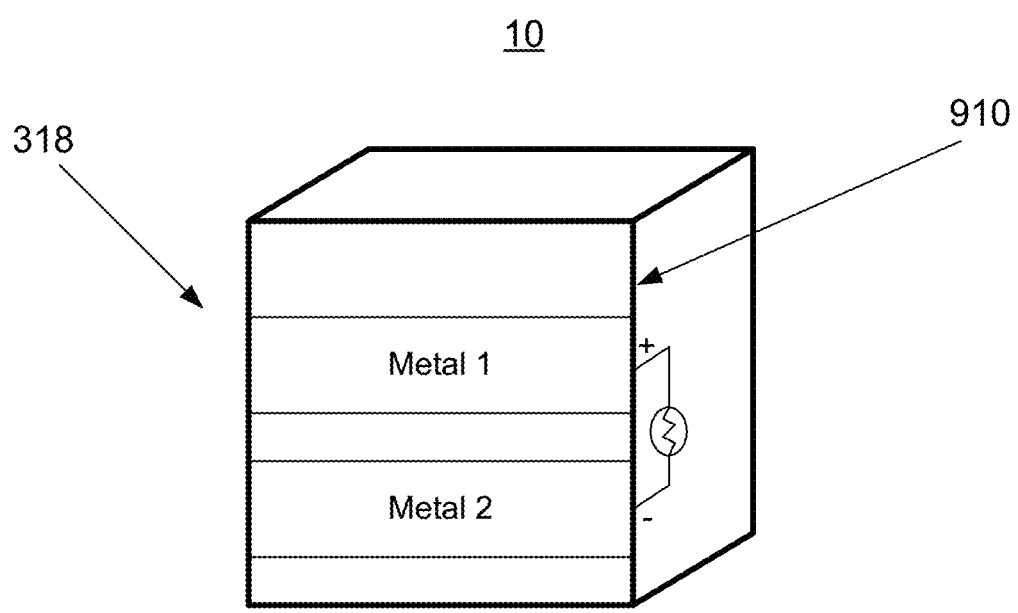
FIG. 9 is a schematic diagram of a microsensor including an electrochemical energy harvester module.

Referring to FIG. 9, a self-powered microsensor 10 including one aspect of an electrochemical energy harvester module 318 is generally illustrated. The electrochemical energy harvester module 318 may be formed by two dissimilar metals (e.g., copper and aluminum) on an outer surface or skin 910 (e.g., in grooves) of the microsensor 10. When these metals contact an ionic solution during use, an electrochemical cell is formed, this is capable of supplying sufficient voltage to power the microsensor 10. Although the metals may eventually corrode, ceasing operation of electrochemical energy harvester module 318, dissolvable coatings may be used to delay activation of the electrochemical energy harvester module 318 as described above.

Using microsensors, consistent with embodiments disclosed herein, provides advantages over other techniques used for tracing such as including radioactive tracer isotopes in the hydrofracturing fluid to determine the injection profile and location of fractures created by hydraulic fracturing. Most of these other techniques are passive, which cannot sense, store, process or transmit the data. The self-powered microsensors provide an advantage by harvesting from the environment to provide energy for a smart sensor system. The microsensors may also be made from 2-D and 1-D nano-materials capable of operating at high temperatures, high pressures, and in corrosive environments. The electronics in these microsensors may be made using high temperature compatible advanced material systems. Accordingly, self-powered microsensors, consistent with embodiments of the present disclosure, are capable of providing the desired measurements while also surviving extremely harsh environments (e.g., high temperature, high pressure, and corrosion).

As used in any embodiment herein, the term "module" may refer to software, firmware and/or circuitry configured to perform one or more operations consistent with the present disclosure. Software may be embodied as a software package, code, instructions, instruction sets and/or data recorded on non-transitory computer readable storage mediums. Firmware may be embodied as code, instructions or instruction sets and/or data that are hard-coded (e.g., non-volatile) in memory devices. "Circuitry", as used in any embodiment herein, may comprise, for example, singly or in any combination, hardwired circuitry, programmable circuitry such as computer processors comprising one or more individual instruction processing cores, state machine circuitry, software and/or firmware that stores instructions executed by programmable circuitry. The modules may, collectively or individually, be embodied as circuitry that forms a part of one or more devices, as defined previously. In some embodiments, the modules described herein may be in the form of logic that is implemented at least in part in hardware to perform various functions consistent with the present disclosure.

Consistent with one aspect, the present disclosure features a delayed-activation sensor system. The delayed-activation sensor system includes at least one microsensor having at least one sensor module for sensing a condition in an environment, and a dissolvable coating encapsulating at least a portion of the at least one sensor module such that the dissolvable coating prevents the at least one sensor module from sensing the condition in the environment. The dissolvable coating may be dissolvable in a fluid in the environment such that the sensor module is activated after being located in the environment for a period of time.

Consistent with another aspect, the present disclosure features a self-powered microsensor for sensing a condition in an environment. The self-powered micro-sensor includes at least one energy harvester module to generate electrical power for the microsensor from the environment, and at least one sensor module electrically coupled to the electrochemical energy harvester module.

Consistent with a further aspect, the present disclosure features a method of in-situ monitoring a hydraulic fracturing operation. The method includes injecting a plurality of dissolvable coated self-powered microsensors into a well bore, dissolving of coating on self-powered microsensors in the well bore, activating the self-powered microsensors, and obtaining measurements from each of the self-powered microsensors.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A delayed-activation sensor system comprising:
   a plurality of microsensors, each of said plurality of microsensors comprising at least one sensor module for sensing a condition in an environment; and
   a group coating encapsulating the plurality of microsensors, the group coating configured to dissolve based on a first condition to expose said plurality of microsensors;
   wherein at least a first one of said plurality of microsensors further comprises a first individual dissolvable coating encapsulating at least a portion of the at least one sensor module, the first individual dissolvable coating configured to dissolve after the group coating and based on a second condition different than the first condition to expose the at least one sensor module to the environment;
   wherein at least a second one of the plurality of microsensors comprises a second individual dissolvable coating encapsulating the second one of the plurality of microsensors, the first and the second individual dissolvable coatings configured to cause said plurality of microsensors to cluster together through electrostatic surface charge, van der Waal forces, electrostatic force, or surface polarity; and
   at least one of a fracking mixture or proppants, wherein the plurality of the microsensors are mixed therein.

2. A method of in-situ monitoring a hydraulic fracturing operation, the method comprising:
   injecting a plurality of self-powered microsensors with a fracking mixture, proppants, or a combination thereof into a well bore, each of said plurality of microsensors comprising at least one sensor module for sensing a condition in an environment,
   wherein a group coating encapsulates the plurality of microsensors, the group coating configured to dissolve based on a first condition to expose said plurality of microsensors;
   wherein at least a first one of said plurality of microsensors comprises a first individual dissolvable coating encapsulating at least a portion of the at least one sensor module, the first individual dissolvable coating configured to dissolve after the group coating and based on a second condition different than the first condition to expose the at least one sensor module to the environment;
   wherein at least a second one of the plurality of microsensors comprises a second individual dissolvable coating encapsulating the second one of the plurality of microsensors, the first and the second individual dissolvable coatings configured to cause said plurality of microsensors to cluster together through electrostatic surface charge, van der Waal forces, electrostatic force, or surface polarity;
   dissolving at least the group coating on the self-powered microsensors in the well bore;
   activating the self-powered microsensors; and
   obtaining measurements from each of the self-powered microsensors.

3. The method of claim 2, wherein the group coating includes a thermal dissolvable coating, the thermal dissolvable coating being selected from a group consisting of a polyamide, polyglycolide or polyglycolic acid, polyvinyl alcohol, polyvinyl pyrrolidone, polyethylene glycol, polystyrenesulfonate, quaternized amine polymers, alkoxomers, and mixtures thereof.

4. The method of claim 2, wherein the group coating includes a water dissolvable coating, the water dissolvable coating being selected from a group consisting of a polymer, PC polymer, cellulose, hydroxyethylcellulose, ethylcellulose, cellulose esthers, resins, and mixtures thereof.

5. The method of claim 2, wherein the group coating includes a pH dissolvable coating, the pH dissolvable coating being selected from a group consisting of a cationic polyacrylamide, acrylate, aminoacrylate, alkyl PEG-20, and mixtures thereof.

6. The method of claim 2, wherein the plurality of microsensors each have dimensions from 1 mm to 20 mm.

7. The method of claim 2, wherein at least one of the plurality of microsensors further comprises a support body for supporting the at least one sensor module, and wherein the first individual dissolvable coating encapsulates the support module.

8. The method of claim 7, wherein the support body has a cuboid shape, and wherein the first individual dissolvable coating forms a spheroid shape.

9. The method of claim 2, wherein at least one of the plurality of microsensors further comprises at least one energy harvester module to generate electrical power for the microsensor from the environment, wherein the at least one energy harvester module is selected from a mechanical energy harvester module, a thermal energy harvester module, or an electrochemical energy harvester module including two dissimilar metals that form an electrochemical cell with a fluid in the environment.

10. The method of claim 2, wherein the first individual dissolvable coating of the first microsensor dissolves slower than the second individual dissolvable coating of the second microsensor such that the first and the second microsensors provide staggered sensor activation at different times.

11. The method of claim 2, further comprising receiving, at one or more supersensors, sensor data from the plurality of microsensors and retransmitting the sensor data to a receiving point outside the environment.

12. The method of claim 2, wherein the measurements are obtained during the hydraulic fracturing.

13. The method of claim 2, wherein the measurements are obtained from within fractures created by the hydraulic fracturing.

14. The method of claim 2, further comprising creating a map during and/or after hydraulic fracturing based on data from the self-powered microsensors.

15. The method of claim 2, further comprising transmitting wireless signals between the microsensors to form a sensor network of microsensor nodes.

16. The method of claim 2, further comprising transmitting signals from the microsensors to a collection point for telemetry.

17. The method of claim 2, further comprising transmitting signals to and/or from the microsensors for determining locations of the microsensors using triangulation.

18. The method of claim 2, wherein the first and the second individual dissolvable coatings are configured to dissolve based on different environmental conditions.

* * * * *